United States Patent [19]

Kerb et al.

[11] Patent Number: 4,591,585
[45] Date of Patent: May 27, 1986

[54] 1-ALKYL-ANDROSTA-1,4-DIENE-3,17-DIONES THEIR PRODUCTION AND PHARMACEUTICAL PREPARATIONS CONTAINING SAME

[75] Inventors: Ulrich Kerb; Gerhard Sauer; Rudolf Wiechert; David Henderson; Yukishige Nishino; Sybille Beier, all of Berlin, Fed. Rep. of Germany

[73] Assignee: Schering Aktiengesellschaft, Berlin and Bergkamen, Fed. Rep. of Germany

[21] Appl. No.: 621,769

[22] Filed: Jun. 18, 1984

[30] Foreign Application Priority Data

Jun. 18, 1983 [DE] Fed. Rep. of Germany ....... 3322285

[51] Int. Cl.$^4$ ............................................. A61K 31/56
[52] U.S. Cl. .................... 514/177; 260/397.3
[58] Field of Search .................... 260/397.3; 514/169, 514/177; 424/238

[56] References Cited

U.S. PATENT DOCUMENTS 4,456,600  6/1984  Wiechert et al. ................. 260/397.4
4,474,701 10/1984  Teichmuller et al. ........... 260/397.4

Primary Examiner—Elbert L. Roberts
Attorney, Agent, or Firm—Millen & White

[57] ABSTRACT

1-Alkyl androsta-1,4-diene-3,17-diones of the formula

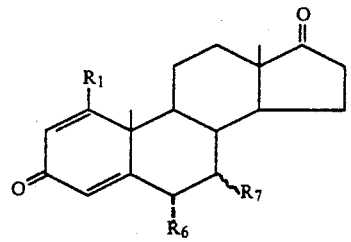

wherein $R_1$ is a methyl, ethyl, hydroxymethyl, $C_1$–$C_3$-alkoxymethyl, or $C_1$–$C_4$-alkanoyloxymethyl group, $R_6$ is a hydrogen atom or a methyl group, and $R_7$ is a hydrogen atom or a methyl group in the 7α- or 7β-position, are useful for fertility control and for the treatment of estrogen-triggered diseases.

17 Claims, No Drawings

1-ALKYL-ANDROSTA-1,4-DIENE-3,17-DIONES THEIR PRODUCTION AND PHARMACEUTICAL PREPARATIONS CONTAINING SAME

BACKGROUND OF THE INVENTION

This invention relates to 1-alkyl-androsta-1,4-diene-3,17-diones of general Formula I, to processes for the production and use thereof, and to pharmaceutical preparations containing them.

SUMMARY OF THE INVENTION

In a composition aspect this invention relates to 1-alkyl-androsta-1,4-diene-3,17-diones of the Formula

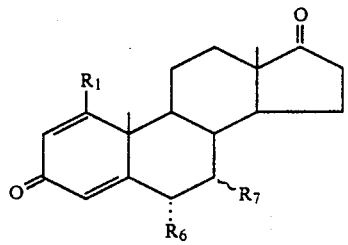

wherein $R_1$ is a methyl, ethyl, hydroxymethyl, $C_1$–$C_3$-alkoxymethyl or $C_1$–$C_4$-alkanoyloxymethyl; $R_6$ is a hydrogen atom or methyl; and $R_7$ is a hydrogen atom or methyl.

In another composition aspect, this invention relates to pharmaceutical compositions comprising a compound of Formula I in admixture with a pharmaceutically acceptable carrier.

In a process aspect, this invention relates to methods for the production of the 1-alkyl steroids of this invention.

In a method of use aspect, this invention relates to the use of the compounds of this invention as aromatase-inhibitors.

DETAILED DISCUSSION

Examples of compounds within the scope of Formula I are those wherein:

(a) both of $R_6$ and $R_7$ are H;
(b) one of $R_6$ and $R_7$ is H and the other is $CH_3$, especially those wherein $R_7$ is $CH_3$;
(c) $R_1$ is $CH_3$, including those of groups (a) and (b);
(d) $R_1$ is $HOCH_2$, including those of groups (a) and (b);
(e) $R_1$ is $CH_3OCH_2$, including those of groups (a) and (b); and
(f) $R_1$ is $CH_3COOCH_2$, including those of groups (a) and (b).

Examples of $R_1$ ether groups are methoxymethyl, ethoxymethyl and straight and branched chain propyloxymethyl and butyloxymethyl.

Examples of $R_1$ ester groups are formyloxymethyl, acetoxymethyl and straight and branched chained propionyloxymethyl and butyryloxymethyl.

The novel compounds of general Formula I inhibit estrogen biosynthesis, which is surprising, since the corresponding androsta-1,4-diene-3,17-diones which are unsubstituted in the 1-position cause a marked rise in the estrogen level.

The conversion of androgens into estrogens plays an important part in the biosynthesis of estrogens. This conversion proceeds by way of a series of reactions called, in combination, "aromatization". The enzyme aromatase is the speed-regulating enzyme in the conversion of androstenedione and testosterone into estrone and estradiol.

The following compounds were examined for aromatase-inhibiting activity and endocrine-pharmacological side effects.

A: 4-Hydroxy-4-androstene-3,17-dione (as a comparison compound in testing for aromatase-inhibiting effect, estrogenic activity, and in the testicle inhibition test).
B: 1-Methylandrosta-1,4-diene-3,17-dione.
C: 1,7α-Dimethylandrosta-1,4-diene-3,17-dione.
D: 1,6α-Dimethylandrosta-1,4-diene-3,17-dione.

1. PMSG Test in Rats to Determine Aromatase-Inhibiting Activity

The influence exerted by test compounds A, B, C, and D on the PMSG (pregnant mare's serum gonadotropin)-stimulated estrogen production was investigated. The secretion of estradiol, increased by treatment with PMSG (control), can be reduced by administration of aromatase inhibitors.

Female rats, age 20 days, were pretreated subcutaneously every 2 days with, in total, $7 \times 100$ I.U. of PMSG. One hour before and 8 hours after the last administration of PMSG ($d_{12}$), the animals received the test compound by injection. The control animals received only the vehicle. Twenty-four hours after the final PMSG administration, the animals were sacrificed. Estradiol in the serum was then determined by radioimmunology. The estradiol concentrations were indicated in nmol/l and the standard deviation was listed.

Variance analysis was used to check the significance of the differences with respect to the control group. The strength of efficacy was determined by regression/covariance analysis.

Compounds B, C, and D of this invention in the same manner as comparison compound A, produce a dose-dependent reduction in the PMSG-elevated estradiol concentration in the peripheral serum in rats (Table 1) with compounds B and D having approximately the same strength of activity as comparison compound A and C being about 6 times more effective than comparison compound A.

TABLE 1

| Effect on Estradiol Concentration in Peripheral Serum in PMSG-Pretreated Rats | | | |
|---|---|---|---|
| | Dose mg/Animal 2 × s.c. | n | Estradiol Concentration nmol/l | Relative Efficacy (A = 1.0) |
| PMSG Control | (0.2 ml Vehicle) | 10 | 4.25 ± 1.57 | |
| A | 0.1 | 10 | 4.31 ± 1.78 | 1.0 |
| | 0.3 | 10 | 3.19 ± 1.31 | |
| | 1.0 | 10 | 1.58 ± 0.92* | |
| | 3.0 | 10 | 1.52 ± 0.74* | |
| B | 0.1 | 10 | 3.53 ± 1.84 | 1.3 |
| | 0.3 | 10 | 2.92 ± 1.09 | |
| | 1.0 | 10 | 1.80 ± 1.13* | |
| | 3.0 | 10 | 0.78 ± 0.18* | |
| C | 0.1 | 10 | 2.21 ± 1.05* | 6.3 |
| | 0.3 | 10 | 0.81 ± 0.32* | |
| | 1.0 | 10 | 0.49 ± 0.21* | |
| | 3.0 | 10 | 0.37 ± 0.11* | |
| D | 0.1 | 10 | 3.73 ± 0.89 | 1.2 |
| | 0.3 | 10 | 2.78 ± 1.17 | |
| | 1.0 | 10 | 1.78 ± 0.67* | |

TABLE 1-continued

Effect on Estradiol Concentration in Peripheral Serum in PMSG-Pretreated Rats

| Dose mg/Animal 2 × s.c. | n | Estradiol Concentration nmol/l | Relative Efficacy (A = 1.0) |
|---|---|---|---|
| 3.0 | 10 | 1.02 ± 0.38* | |

* = Significant difference as compared with PMSG control
n = Number of animals per group 2. Uterus/Vaginal Growth Test in Mice and Rats to Test for Estrogenic Activity Ovariectomized rats (200 g) and mice (30 g), respectively, received subcutaneous administrations of the test compound once daily for 5 days. The control animals received only the vehicle.

One day after the final treatment, the animals were sacrificed. Uterus and vagina were then immediately excised and weighed.

The average value for the organ weight and the standard deviation were determined for each group. The significance of the differences as compared with the control group was examined by variance analysis.

Compound B of this invention (3 and 10 mg/animal/day, 5×s.c.) does not evoke estrogenic activity either in rats or mice (Tables 2 and 3). Comparison compound A, in contrast thereto, leads to a significant increase in weights of the uteri with a dosage of 3 and 10 mg/animal/day (5×s.c.).

3. Testicle Inhibition Test In Rats to Determine Antigonadotropic Activity

Infantile male rats (30 g) were treated once daily for 12 days with the test compound by subcutaneous administration. One day after the final treatment, the animals were sacrificed and the testes were weighed. The control animals received only the vehicle.

For control purposes, the organ weights of the prostates, seminal vesicles, and adrenal glands were determined.

The organ weights were converted to mg/100 g body weight. For each group, the average value and the standard deviation were calculated.

The significance of the differences with respect to the control was checked by variance analysis.

TABLE 2

Estrogen Test on Ovariectomized Mice

| | Dose mg/Animal/d s.c. | Organ Weight [mg] | |
|---|---|---|---|
| | | Uterus | Vagina |
| $E_2$ | 0.00003 | 126.5 ± 20.5* | 55.9 ± 7.8 |
| A | 3 | 48.4 ± 8.8* | 16.6 ± 3.3 |
| | 10 | 64.7 ± 13.1* | 23.1 ± 4.4 |
| B | 3 | 23.8 ± 6.7 | 17.7 ± 4.5 |
| | 10 | 13.7 ± 3.0 | 10.6 ± 1.5 |
| Oil Control | — | 32.3 ± 9.2 | 23.5 ± 6.5 |

* = Significant difference as compared with control
$E_2$ = Estradiol

TABLE 3

Estrogen Test on Ovariectomized Rats

| | Dose mg/Animal/d s.c. | Organ Weight [mg] | |
|---|---|---|---|
| | | Uterus | Vagina |
| $E_2$ | 0.0001 | 214.4 ± 25.1* | 102.3 ± 11.8* |
| A | 3 | 94.3 ± 21.9 | 52.9 ± 5.7 |
| | 10 | 131.9 ± 21.0 | 68.1 ± 6.2 |
| B | 3 | 85.0 ± 7.6 | 55.8 ± 7.4 |
| | 10 | 87.4 ± 21.1 | 56.6 ± 9.4 |
| Oil Control | — | 94.5 ± 22.8 | 66.0 ± 20.5 |

* = Significant difference as compared with control
$E_2$ = Estradiol

In the testicle inhibition test, compound B of this invention, at the tested dosages (1 and 3 mg/animal/day 12×s.c.), shows, no effect on the testicle weights (no antigonadotropin activity) but produces, at a dosage of 1 mg/animal/day, a slight reduction in seminal vesicle weights. In contrast thereto, comparison compound A produces a significant reduction in the organ weights of the testicles, seminal vesicles and adrenal glands.

In the anabolic/androgen test, compound B of this invention has no effect on the fresh weights of seminal vesicles, prostate, m. [musculus]levator ani, and adrenal glands.

It can be seen from tests (1) through (3) that the compounds of this invention are strong aromatase inhibitors which are extremely neutral from the viewpoint of endocrine pharmacology.

As aromatase inhibitors, the novel compounds of general Formula I are suitable for inhibiting estrogen biosynthesis and consequently for the treatment of diseases caused by or dependent upon estrogens.

For example, an excess of estrogen is frequently found in women who are in menopause, with the associated risk of contracting breast cancer. In men, increased estrogen production and a raised estrogen/androgen ratio leads to gynecomastia and hyperplasia of the prostate.

Consequently, the compounds are suitable for treatment of breast cancer and other estrogen-induced or -stimulated tumors.

As aromatase inhibitors, they are also advantageously suited for prophylactic and/or therapeutic treatment of prostate hyperplasia, as described, e.g., in U.S. Ser. Nos. 448,672 and 448,673, both filed on Dec. 10, 1982, and both of whose disclosures are incorporated by reference herein.

The novel compounds are also valuable for affecting fertility, for example for treatment of male infertility resulting from elevated estrogen levels. Furthermore, the compounds can be utilized as antifertility agents, e.g., to prevent ovulation or implantation in women of childbearing age.

TABLE 4

Testicle Inhibition Test in Rats

| | Dose mg/Animal/Day | n | Organ Weights mg/100 g Body Weight | | | |
|---|---|---|---|---|---|---|
| | | | Testicles | Seminal Vesicle | Prostate | Adrenal Gland |
| B | 1 | 10 | 891 ± 75 | 12.8 ± 4.4* | 40.1 ± 6.7 | 32.4 ± 5.4 |
| | 3 | 10 | 913 ± 70 | 14.5 ± 3.6 | 42.0 ± 7.7 | 27.4 ± 3.4 |
| A | 1 | 10 | 779 ± 125* | 9.6 ± 2.6* | 43.3 ± 9.8 | 23.9 ± 2.9* |
| | 3 | 10 | 633 ± 50* | 14.4 ± 3.0 | 57.5 ± 11.7 | 26.1 ± 4.3 |

TABLE 4-continued

| | Testicle Inhibition Test in Rats | | | | |
|---|---|---|---|---|---|
| Dose | | Organ Weights mg/100 g Body Weight | | | |
| | mg/Animal/Day | n | Testicles | Seminal Vesicle | Prostate | Adrenal Gland |
| Control (Oil) | — | 10 | 1012 ± 129 | 17.8 ± 5.1 | 51.3 ± 17.0 | 30.3 ± 3.1 | n = Number of animals per group
* = Significant difference with respect to control The compounds can be administered orally or parenterally, for example intraperitoneally, intramuscularly, subcutaneously, or percutaneously. The compounds can also be implanted in tissue.

The amount of compound to be administered varies within a wide range and can cover any effective quantity. Depending on the condition to be treated and the method of administration, the amount of compound administered can be 0.01-100 mg/kg body weight, preferably 0.1-20 mg/kg body weight, per day.

For oral administration, suitable are capsules, pills, tablets, dragees, etc. The dosage units can contain, besides the active ingredient, a pharmaceutically acceptable excipient, such as, for example, amylose, sugar, sorbitol, gelatin, lubricants, silicic acid, talc, etc. The individual dosage units for oral administration can contain, for example, 10-100 mg of the active agent (aromatase inhibitor).

For parenteral administration, the active agents can be dissolved or suspended in a physiologically compatible diluent. Oils, with or without the addition of a solubilizer, are utilized very frequently as the diluents. Examples for oils that are utilized are olive oil, peanut oil, cottonseed oil, soybean oil, castor oil, and sesame oil.

The compounds can also be used in the form of a depot injection or an implant preparation, which can be formulated so that timed release of active compound is made possible.

Implants can contain, as the inert materials, for example, biologically degradable polymers or synthetic silicones, e.g., silicone rubber. The active agents furthermore can be incorporated into a plaster for percutaneous administration.

This invention, in one aspect, relates to pharmaceutical preparations containing a compound of general Formula I.

The novel compounds of general Formula I can be produced according to the following reaction schemes:

(a) in a 17-hydroxy steroid of general Formula II

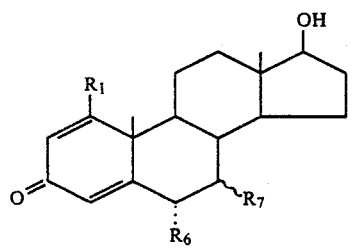
(II)

wherein $R_1$, $R_6$ and $R_7$ have the values given for Formula I, the 17-hydroxy groups is oxidized to the 17-oxo group; or (b) a steroid which is saturated in the A-ring or monounsaturated, according to general Formula III

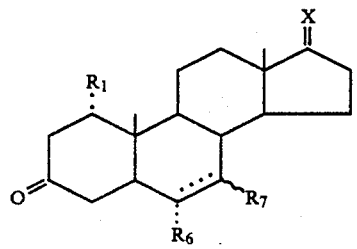
(III)

wherein X is O, H(OH), or H(OAc), Ac standing for a lower acyl group of 1-4 carbon atoms, $R_1$, $R_6$ and $R_7$ have the values given for Formula I, and ------- is a $\Delta^4$-double bond which may be present or absent, is dehydrogenated in the 1,2-position, e.g., when the $\Delta^4$-double bond is present, or in both the 1,2- and 4,5-positions, and a free or liberated 17-hydroxy group is oxidized; or (c) a steroid, saturated in the A-ring, of general Formula IV

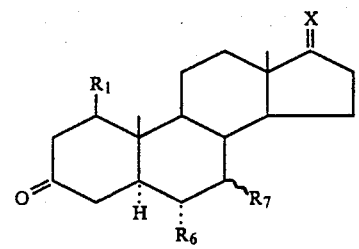
(IV)

wherein X is O, H(OH), or H(OAc), Ac being lower acyl of 1-4 carbon atoms, and $R_1$, $R_6$ and $R_7$ have the values given for Formula I, is dehydrogenated in the 1,2- and 4,5-positions, and a free or liberated 17-hydroxy group is oxidized; or (d) the alkanoyloxy group of a 1-alkanoyloxymethyl steroid of general Formula I'

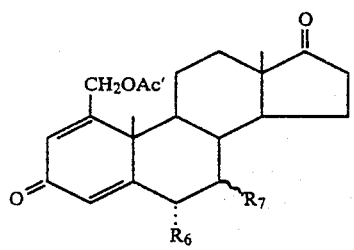
(I')

wherein Ac' is alkanoyl of 1-4 carbon atoms and $R_6$ and $R_7$ have the values given for Formula I, is saponified and optionally the liberated hydroxy group in the 1-hydroxymethyl steroid is converted into a $C_{1-3}$ alkyl ether or a $C_{1-4}$ alkanoyl ester that is different from that represented by —OAc'.

Reactions (a) through (d) take place according to known methods of steroid chemistry.

The oxidation set forth in process version (a) can be conducted in a manner known per se, for example with chromic acid reagents (Jones' reagent or chromic acid-pyridine) or with pyridinium dichromate or chlorochromate.

The 1,2-dehydrogenation according to process (b) can take place by means of known methods with dehydrogenation agents such as selenium dioxide or dichlorodicyanobenzoquinone.

Double bonds in the 1,2- and 4,5-positions can be introduced simultaneously, for example by bromination to the 2,4-dibromo-3-ketone and dehydrobromination of the dibromide with lithium carbonate or calcium carbonate and lithium bromide in dimethylformamide.

A 1-hydroxymethyl group liberated during the reaction can subsequently be esterified or etherified, and a liberated 17-hydroxy group can subsequently be oxidized.

Esterification of the 1-hydroxymethyl group in the presence of a 17-hydroxy group takes place preferably with lead diacetate and acetic anhydride in dimethylformamide.

Oxidation of the 17$\beta$-hydroxy group is accomplished by following process version (a).

For the dehydrogenation according to process version (c), the chemical dehydrogenation agents as well as microbiological dehydrogenation can be employed. Suitable microorganisms for introduction of the 1,2- and 4,5-double bonds are, for example, schizomycetes, for example Arthrobacter simplex (ATCC 6946), Bacillus lentus (ATCC 13805), or Bacillus sphaericus (ATCC 7055).

Saponification of a 1-alkanoyloxymethyl group according to process (d) can take place with an inorganic base in an alcoholic solution and the optionally subsequent reesterification is preferably conducted with the corresponding acid anhydride in the presence of organic bases.

In order to convert the 1-hydroxymethyl steroid of general Formula I into the corresponding 1-alkoxymethyl ether, a preferred embodiment provides to react the 1-hydroxymethyl steroid with p-toluenesulfonic acid chloride and pyridine to the 1-tosyloxymethyl steroid, and then with alkali alcoholate to the 1-alkoxymethyl steroid.

Contemplated equivalents of the compounds of this invention are aromatase inhibiting compounds otherwise corresponding to those of Formula I wherein $R_1$ is a hydroxymethyl group esterified or etherified with another ester or ether group, e.g., higher alkoxy or alkanoyloxy.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

6.01 g of 17$\beta$-hydroxy-1-methylandrosta-1,4-dien-3-one is dissolved in 100 ml of acetone. At room temperature, 22 ml of a chromic acid solution (prepared from 6.67 g of CrO$_3$, 6 ml of concentrated H$_2$SO$_4$, replenished with water to 100 ml) is added dropwise to this solution. The mixture is stirred for one hour and then precipitated into ice water; the product is suctioned off and dried, thus obtaining after recrystallization from acetone/hexane 5.25 g of 1-methylandrosta-1,4-diene-3,17-dione, mp 165°–166° C.

EXAMPLE 2

30 g of 1$\alpha$,7$\alpha$-dimethyl-4-androstene-3,17-dione is heated under reflux in 700 ml of dioxane with 30 g of dichlorodicyanobenzoquinone for 8 hours. After cooling, the product is suctioned off from undissolved matter, washed with dioxane, and the filtrate concentrated under vacuum. The residue is chromatographed on silica gel and recrystallized from acetone/hexane, thus obtaining 18 g of 1,7$\alpha$-dimethylandrosta-1,4-diene-3,17-dione, mp 148°–151° C.

The following compounds are prepared analogously:

1,7$\beta$-dimethylandrosta-1,4-diene-3,17-dione, mp 196°–197° C., from 1$\alpha$,7$\beta$-dimethyl-4-androstene-3,17-dione;

1,6$\alpha$-dimethylandrosta-1,4-diene-3,17-dione, mp 234°–235° C., from 1$\alpha$,6$\alpha$-dimethyl-4-androstene-3,17-dione;

1-ethylandrosta-1,4-diene-3,17-dione, mp 175°–176° C., from 1$\alpha$-ethyl-4-androstene-3,17-dione.

EXAMPLE 3

9.1 g of 1$\alpha$-acetoxymethyl-17$\beta$-acetoxy-5$\alpha$-androstan-3-one (mp 193°–194° C.) [prepared from 3,3-ethylenedioxyl-1-methylene-5$\alpha$-androstan-17$\beta$-ol ("Naturwissenschaften" [Natural Sciences 51: 86 (1963)) by hydroboration, acetylation, and ketal cleavage] is dissolved in 90 ml of glacial acetic acid. To this solution is added dropwise 3.2 ml of bromine in 25 ml of glacial acetic acid, and the mixture is agitated for 10 minutes. After precipitation in ice water which contains sodium sulfite, the product is suctioned off, washed with water, and dried. 16.5 g of crude dibromide is stirred in 100 ml of dimethylformamide with 10 g of lithium bromide and 20 g of calcium carbonate for 3.5 hours at a bath temperature of 120° C. After cooling, the inorganic salts are suctioned off and washed with 150 ml of methanol. The filtrate is combined with 6 g of potassium hydroxide in 20 ml of water and stirred for 16 hours at room temperature. The reaction solution is poured into ice water, the product is suctioned off and dried. The crude 1-hydroxymethyl-17$\beta$-hydroxyandrosta-1,4-dien-3-one (7.5 g) is dissolved in 100 ml of dimethylformamide, combined with 1 g of lead diacetate and 15 ml of acetic anhydride and stirred for 6.5 hours at room temperature. After precipitating in water and removal of the product by vacuum filtering, oxidation is carried out with chromic acid as described in Example 1. Recrystallization from acetone/hexane yields 2.3 g of 1-acetoxymethylandrosta-1,4-diene-3,17-dione, mp 121°–123° C.

EXAMPLE 4

2.2 g of 1-acetoxymethylandrosta-1,4-diene-3,17-dione is stirred under argon gas atmosphere in 20 ml of methylene chloride and 25 ml of methanol with 250 mg of potassium hydroxide at 0° to 5° C. for 5 hours. The mixture is then neutralized with acetic acid, concentration, and precipitated into water. The product is suctioned off, washed with water, and dried. Recrystallization from acetone/hexane yields 1.7 g of 1-hydroxymethylandrosta-1,4-diene-3,17-dione, mp 201°–202° C.

EXAMPLE 5

500 mg of 1-hydroxymethylandrosta-1,4-diene-3,17-dione is dissolved in 5 ml of pyridine, cooled to 0° C., combined with 350 mg of p-toluenesulfonyl chloride, and stirred at room temperature for 3 hours. After water precipitation of the product, suctioning off, washing with water, and drying, 700 mg of crude tosylate is obtained. This crude product is agitated in 5 ml of toluene with 500 mg of potassium ethylate for 5 hours at 20° C. Subsequently the mixture is diluted with ether, washed with dilute hydrochloric acid and with water, and concentrated under vacuum. Chromatography on silica gel and recrystallization from hexane/acetone yields 325 mg of 1-ethoxymethylandrosta-1,4-diene-3,17-dione, mp 95°–98° C.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. 1-Alkyl-androsta-1,4-diene-3,17-diones of the formula

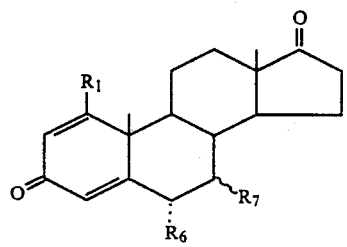

wherein
 $R_1$ is a methyl, ethyl, hydroxymethyl, $C_1$–$C_3$-alkoxymethyl or $C_1$–$C_4$-alkanoyloxymethyl;
 $R_6$ is a hydrogen atom or methyl; and
 $R_7$ is a hydrogen atom or methyl.

2. 1-Methylandrosta-1,4-diene-3,17-dione, a compound of claim 1.

3. 1,7α-Dimethylandrosta-1,4-diene-3,17-dione and 1,7β-dimethylandrosta-1,4-diene-3,17-dione, a compound of claim 1.

4. 1,6α-Dimethylandrosta-1,4-diene-3,17-dione, a compound of claim 1.

5. 1-Ethylandrosta-1,4-diene-3,17-dione, a compound of claim 1.

6. 1-Acetoxymethylandrosta-1,4-diene-3,17-dione, a compound of claim 1.

7. 1-Hydroxymethylandrosta-1,4-diene-3,17-dione, a compound of claim 1.

8. 1-Ethoxymethylandrosta-1,4-diene-3,17-dione, a compounds of claim 1.

9. A pharmaceutical composition comprising a compound of claim 1 in admixture with a pharmaceutically acceptable carrier.

10. A compound of claim 1, wherein $R_1$ is hydroxymethyl.

11. A compound of claim 1, wherein $R_1$ is $C_{1-3}$-alkoxymethyl.

12. A compound of claim 1, wherein $R_1$ is $C_{1-4}$-alkanoyloxymethyl.

13. A composition of claim 1, wherein the amount of said compound is 10–100 mg.

14. A method of inhibiting estrogen biosynthesis in a patient comprising administering an effective amount of a compound of claim 1.

15. A method of inhibiting aromatase activity in a patient comprising administering an effective amount of a compound of claim 1.

16. A method of treating an abnormally increased estrogen level in a patient comprising admixing an effective amount of a compound of claim 1.

17. A method of treating benign prostatic hyperplasia in a patient comprising administering an effective amount of a compound of claim 1.

* * * * *